(12) United States Patent
Tang

(10) Patent No.: US 7,694,677 B2
(45) Date of Patent: Apr. 13, 2010

(54) NOISE SUPPRESSION FOR AN ASSISTED BREATHING DEVICE

(75) Inventor: David Tang, Oakland, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 1019 days.

(21) Appl. No.: 11/340,094

(22) Filed: Jan. 26, 2006

(65) Prior Publication Data
US 2007/0169781 A1    Jul. 26, 2007

(51) Int. Cl.
*A62B 18/02* (2006.01)
(52) U.S. Cl. .................................................. 128/204.18
(58) Field of Classification Search ............ 128/203.24, 128/204.18, 204.21, 204.22, 204.23, 867, 128/206.15, 200.24, 203.13, 203.14
See application file for complete search history.

(56) References Cited

U.S. PATENT DOCUMENTS

| 3,545,566 | A | | 12/1970 | Abrahamsson | 181/50 |
| 4,316,523 | A | * | 2/1982 | Boretti | 181/226 |
| 5,526,805 | A | * | 6/1996 | Lutz et al. | 128/204.18 |
| 5,809,996 | A | | 9/1998 | Alldredge | 128/200.23 |
| 2005/0150801 | A1 | | 7/2005 | Tippey | 206/440 |
| 2006/0005835 | A1 | * | 1/2006 | Berthon-Jones | 128/204.23 |

FOREIGN PATENT DOCUMENTS

EP    1555400 A1    7/2005
WO   2005097244 A1   10/2005

OTHER PUBLICATIONS

International Search Report with Written Opinion PCT/US2007/061047, 12 pages, Jun. 18, 2007.

* cited by examiner

*Primary Examiner*—Steven O Douglas

(57) ABSTRACT

A system for delivering a supply of pressurized gas to a user may include a blower and a noise suppression portion. The blower may include an intake portion and an outlet portion for supplying the pressurized gas to the user. The noise suppression portion may define a conduit therethrough having an intake portion and an outlet portion in communication with the intake portion of said blower. The noise suppression portion may be moveable between a first configuration and a second configuration such that at least one exterior dimension of the device is reduced when the noise suppression portion is moved from the first configuration to the second configuration.

30 Claims, 9 Drawing Sheets

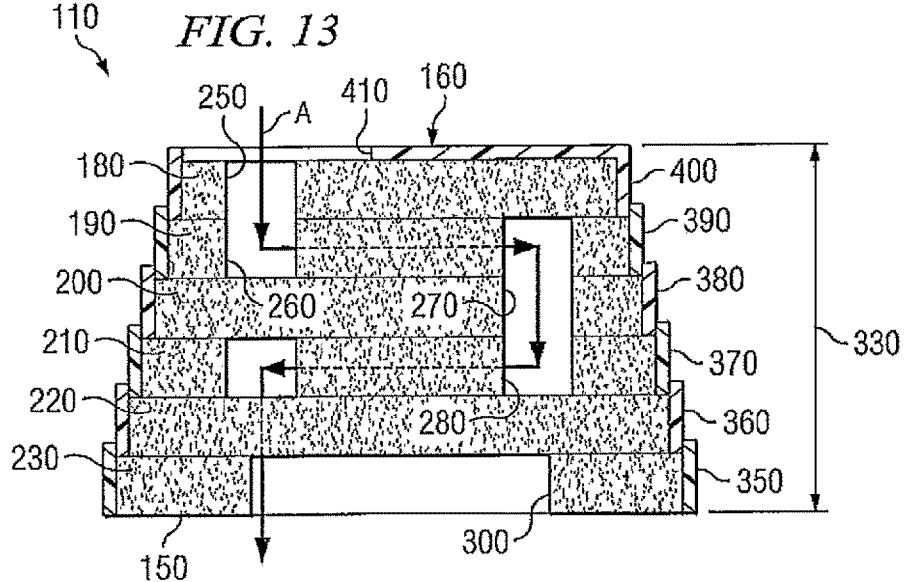
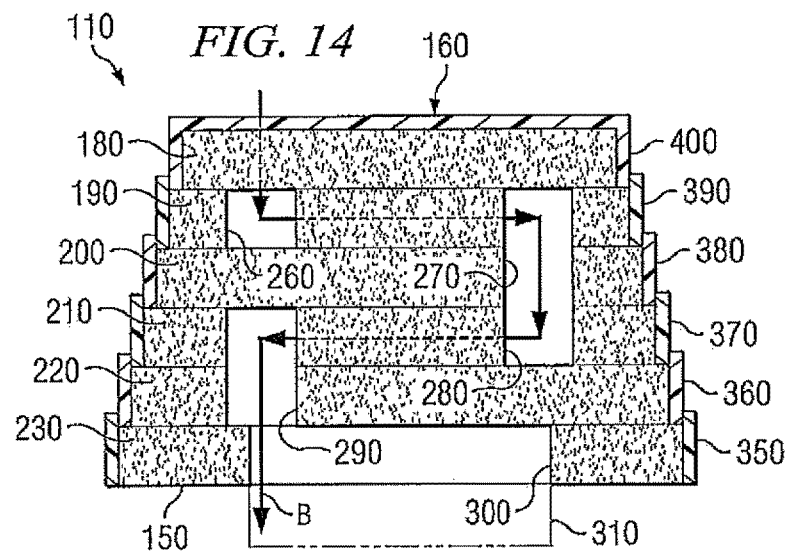
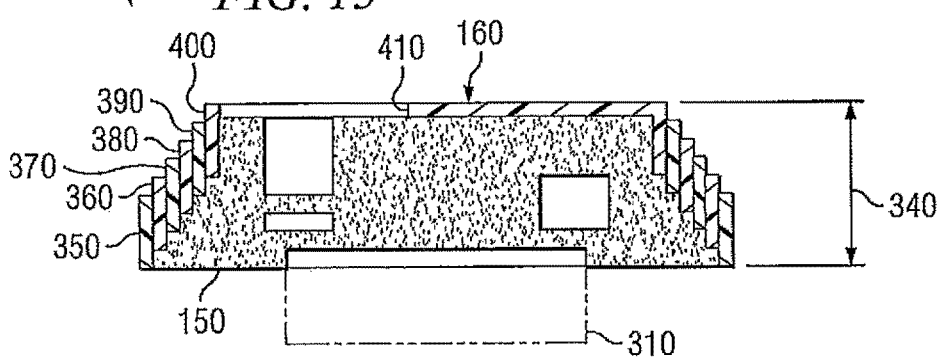

NOISE SUPPRESSION FOR AN ASSISTED BREATHING DEVICE

TECHNICAL FIELD

The present disclosure is related to medical devices, e.g., systems and methods of noise suppression for an assisted breathing device.

BACKGROUND

Problem snoring in subjects is often caused by an obstruction to the free flow of air through the passages at the back of the mouth and/or nose. Recently, the adverse medical effects of snoring and its association with Obstructive Sleep Apnea (OSA) and Upper Airway Resistance Syndrome (UARS) have been recognized. Various methods have been used to alleviate snoring or OSA. Such techniques include, e.g., behavior modification, sleep positioning, assisted breathing devices, jaw adjustment techniques, and surgical procedures such as Uvulopalatopharyngoplasty (UPPP), and laser assisted Uvula Palatoplasty (LAUP), for example.

Subjects who are prescribed assisted breathing devices, e.g., CPAP devices or Bi-level devices, use these devices to aid their breathing during sleep. A nasal CPAP device may deliver air into the subject's airway through a specially designed nasal mask or pillows. The device may create a flow of air having sufficient pressure to keep the airway open when the subject inhales. A blower is often provided in these devices to produce the desired airflow. In order to operate at an acceptably low sound level, and to avoid disturbing the subject's sleep, a noise suppression device may be provided to dampen the noise generated by the blower. For example, in some current CPAP and Bi-level devices, about 40% of the volume of the device is comprised of acoustic foam and empty volume provided for acoustic dampening.

Subjects may use these devices every night to achieve satisfactory sleep patterns regardless of whether they are at home or traveling. Thus, subjects who travel are generally required to bring a portable device with them in order to continue breathing assistance. For such traveling subjects, the size of the device may be an important consideration (e.g., due to limited luggage space). To illustrate the size of an example portable CPAP device, the Puritan Bennett GK 420 CPAP, which is illustrated as device "P" in FIGS. 1 and 3, measures approximately 7.5"×5.5"×3".

SUMMARY

Accordingly, there is a need for noise suppression systems for use in assisted breathing devices, e.g., CPAP or bi-level devices, that overcome the limitations of prior devices and/or that facilitate the portable use of such devices (e.g., for traveling).

In accordance with one embodiment of the present disclosure, a system for delivering a supply of pressurized gas to a user may include a blower and a noise suppression portion. The blower may include an intake portion and an outlet portion for supplying the pressurized gas to the user. The noise suppression portion may define a conduit therethrough having an intake portion and an outlet portion in communication with the intake portion of said blower. The noise suppression portion may be moveable between a first configuration and a second configuration such that at least one exterior dimension of the device is reduced when the noise suppression portion is moved from the first configuration to the second configuration. In accordance with another embodiment of the present disclosure, the system may further comprise a tube having first and second ends. The first end of the tube may be adapted for connection to the outlet portion of the blower, and the second end of the tube may be adapted for connection to a mask. According to a further embodiment of the present disclosure, a system may further comprise a mask adapted for connection to the second end of the tube, e.g., the mask may comprise a nasal mask; however, any mask may be utilized with the systems of the present disclosure.

In accordance with another embodiment of the present disclosure, an apparatus for reducing noise generated by a breathing device for delivering gas to a user is provided. The apparatus may include a body and a conduit defined within the body. The body may be moveable between a first configuration and a second configuration such that at least one exterior dimension of the body is reduced when the body is moved from the first configuration to the second configuration. The conduit may include an intake portion and an outlet portion, the outlet portion being in communication with the intake portion of a gas supply device.

In accordance with yet another embodiment of the present disclosure, a method includes providing a device for delivering a supply of pressurized gas to a user, the device including a blower having an intake portion and an outlet portion for supplying the pressurized gas to the user, and a noise suppression portion defining a conduit therethrough, said conduit having an outlet portion in communication with the intake portion of said blower. The method further includes moving said noise suppression portion of said device between a first configuration and a second configuration such that at least one exterior dimension of the device is reduced when the noise suppression portion is moved from the first configuration to the second configuration.

In accordance with yet another embodiment of the present disclosure, a system for delivering a supply of pressurized gas to a user includes blowing means and noise suppression means. The blowing means may include an intake portion and an outlet portion for supplying the pressurized gas to the user. The noise suppression means may define a conduit therethrough having an intake portion and an outlet portion, the outlet portion of said conduit in communication with the intake portion of said blower. The noise suppression means may be moveable between a first configuration and a second configuration such that at least one exterior dimension of the device is reduced when the noise suppression means is moved from the first configuration to the second configuration. According to another embodiment, a system of the present disclosure may further comprise a fluid communication means, e.g., a tube or conduit, having first and second ends. The first end of the fluid communication means may be adapted for connection to the outlet portion of the blower, and the second end of the fluid communication means may be adapted for connection to a mask. According to one embodiment, a system of the present disclosure may further comprise a mask, e.g., a nasal mask; however, any mask may be utilized with systems of the present disclosure.

It should be understood that various changes, substitutions and alternations can be made herein without departing from the spirit and scope of the disclosure as illustrated by the following claims.

BRIEF DESCRIPTION OF THE DRAWINGS

Some embodiments of the disclosure may be understood by referring, in part, to the following description and the accompanying drawings, in which like reference numbers refer to the same or like parts and wherein:

FIG. 13 is a sectional side view taken through lines 13-13 of FIGS. 7-12 of a portion of a breathing apparatus in an uncompressed configuration, in accordance with an embodiment of the present disclosure;

FIG. 14 is a sectional side view taken through lines 14-14 of FIGS. 7-12 of a portion of a breathing apparatus in an uncompressed configuration, in accordance with an embodiment of the present disclosure;

FIG. 15 is a sectional side view of a portion of a breathing apparatus in a compressed configuration, in accordance with an embodiment of the present disclosure;

DETAILED DESCRIPTION

Selected embodiments of the disclosure may be understood by reference, in part, to FIGS. 1-19. Although the following discussion focuses on a noise suppression device or system for an assisted breathing device, e.g., a CPAP device, it should be understood that the disclosed subject matter may be used in connection with any medical or therapeutic device for transporting gas (e.g., air and/or oxygen), where sound reduction and/or compact size may be relevant considerations.

Figure 1:
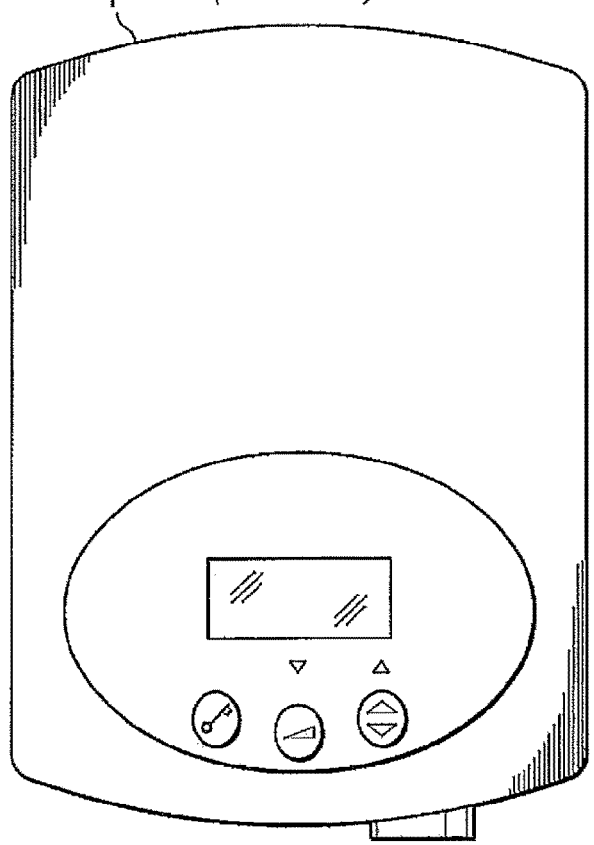
FIG. 1 is a top view of a prior art assisted breathing device P.
Figure 2:
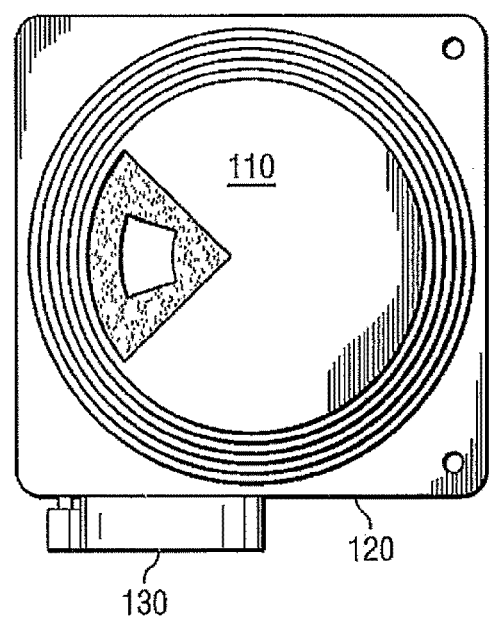
FIG. 2 is a top view of an example assisted breathing device, depicted at approximately the same scale as FIG. 1, in accordance with an embodiment of the present disclosure.
Figure 3:
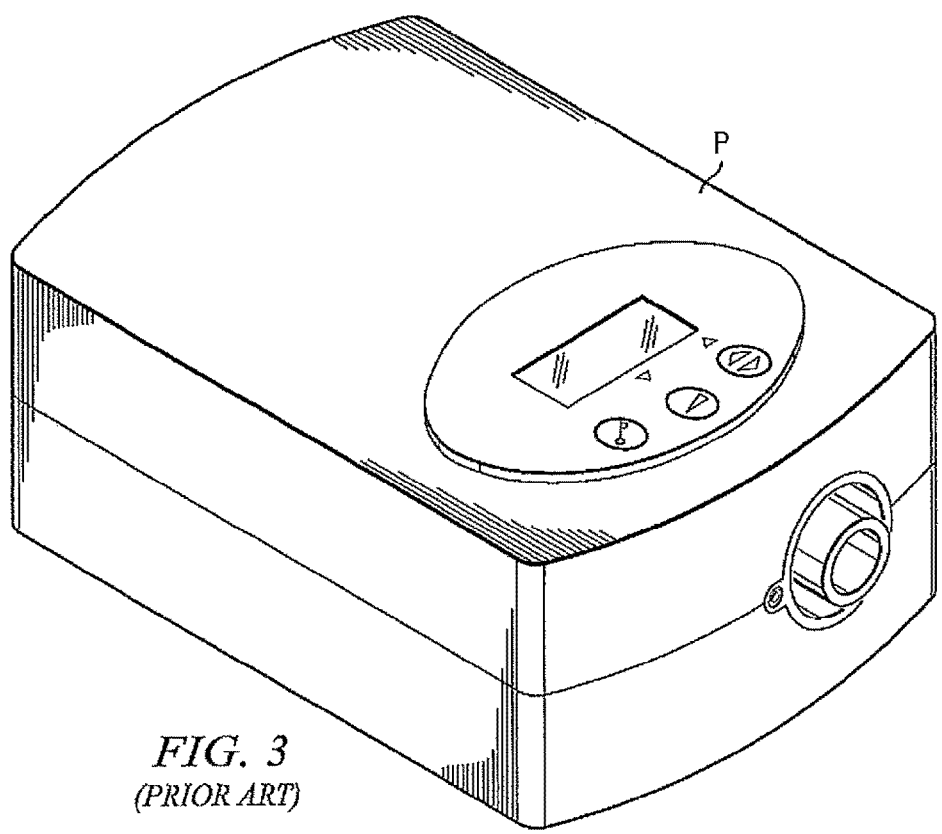
FIG. 3 is a perspective view of the prior art assisted breathing device P of FIG. 1.
Figure 4:
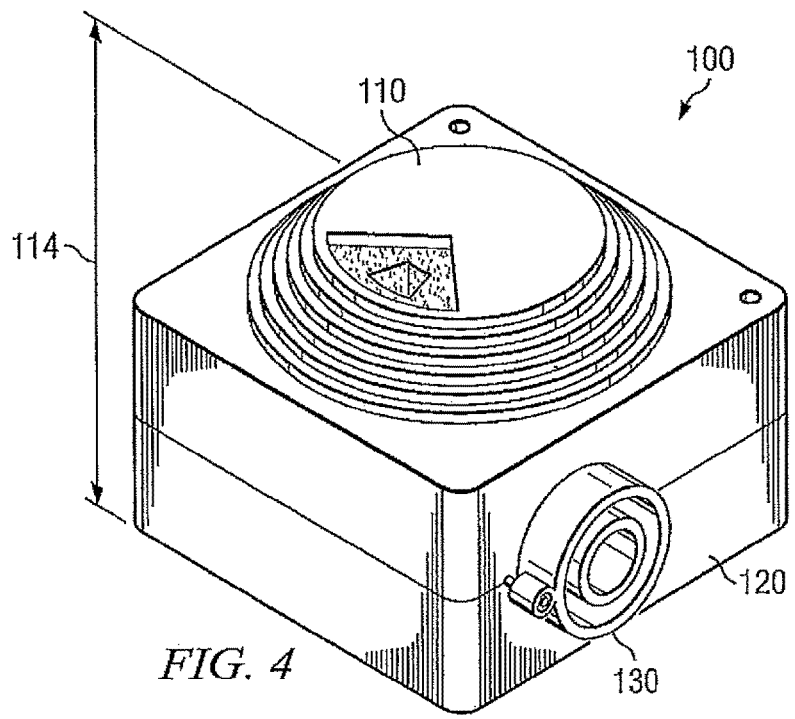
FIG. 4 is a perspective view of the breathing apparatus of FIG. 2 in a compressed configuration, depicted at approximately the same scale as FIG. 3, in accordance with an embodiment of the present disclosure.
Figure 5:
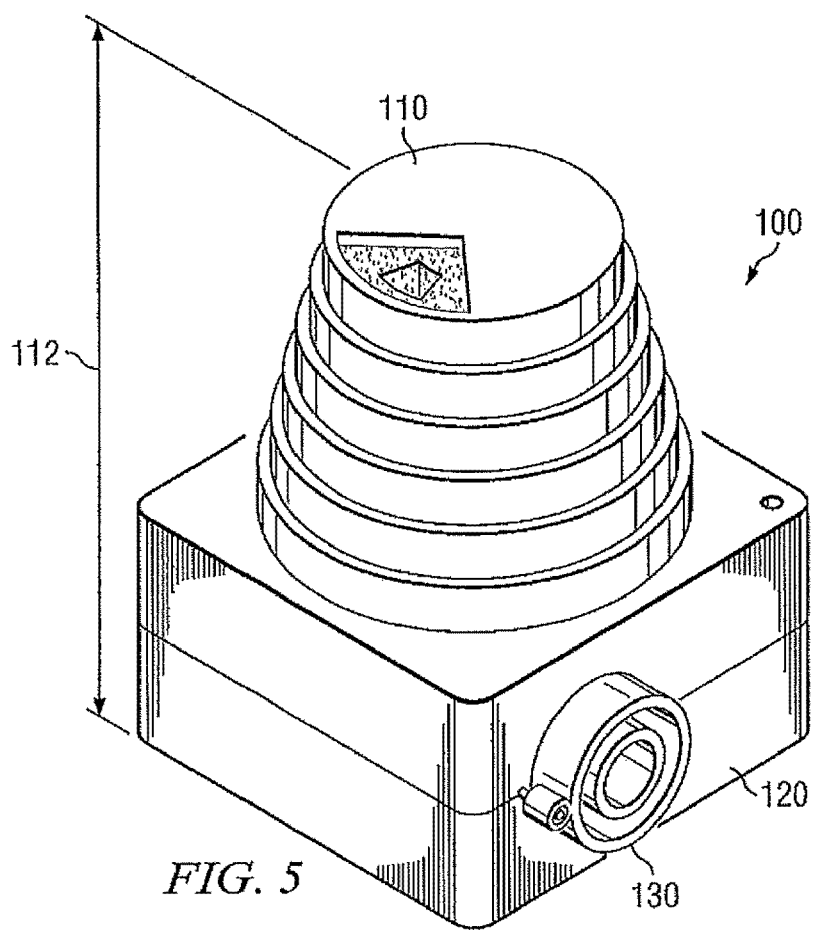
FIG. 5 is a perspective view of the breathing apparatus of FIG. 2 in an uncompressed configuration, depicted at approximately the same scale as FIG. 3, in accordance with an embodiment of the present disclosure.

According to an embodiment of the disclosure, a system 100 may include an acoustic dampening design that reduces the transport size of a device. As illustrated in FIGS. 2, 4, and 5, system 100 may include a noise suppression portion 110, a body portion 120, and a port 130 for connecting to an gas hose which may supply the pressurized gas to the nasal mask (not shown). The noise suppression portion 110 may be moveable between a compressed configuration useful during transport (see, FIG. 4) and a relaxed or uncompressed configuration during system use (see, FIGS. 2 and 5.) As can be seen by comparison with prior devices, system 100 may provide a substantial reduction in the overall size of the device (for example, compare the devices shown in FIGS. 3 and 4). As discussed herein above, a prior device, e.g., the Puritan Bennett GK 420 CPAP has overall dimensions of 7.5"×5.5"×3". In comparison, in certain embodiments, the noise suppression system disclosed herein may permit devices to be relatively smaller and also maintain low noise levels during use. For example, an example system 100 including a noise suppression system described herein may have dimensions of approximately 5"×4.5"×2.5".

Figure 6:
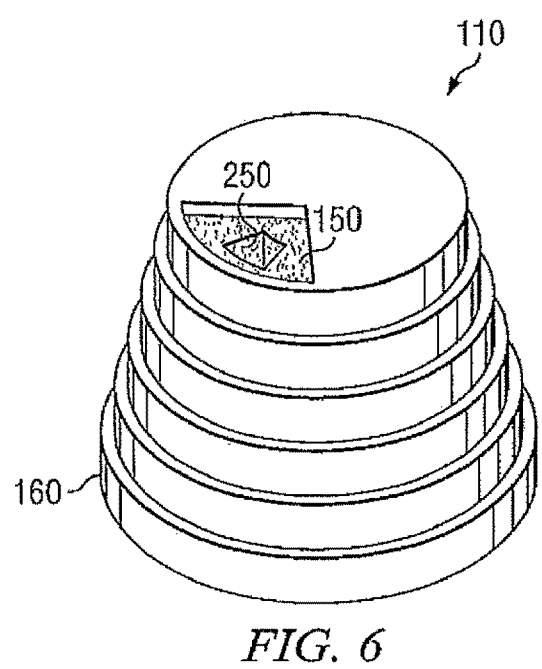
FIG. 6 is a perspective view from above of a portion of a breathing apparatus in an uncompressed configuration, in accordance with an embodiment the present disclosure.

In some embodiments, system 100 may be provided with a noise suppression portion 110 that may be compressible to reduce the travel size of system 100. Referring to FIGS. 4 and 5, compression of the noise suppression portion 110 may result in the reduction of one or more exterior dimensions of system 100. For example, the height 112 of system 100 in the uncompressed configuration, e.g., about 4.75 inches as shown in FIG. 5, may be reduced to a height 114 in the compressed configuration, e.g., about 3.5 inches. In some embodiments, the noise suppression portion 110 may include a compressible foam (or other) structure 150 within a collapsible conical shell 160, as shown in FIG. 6.

Figure 7:
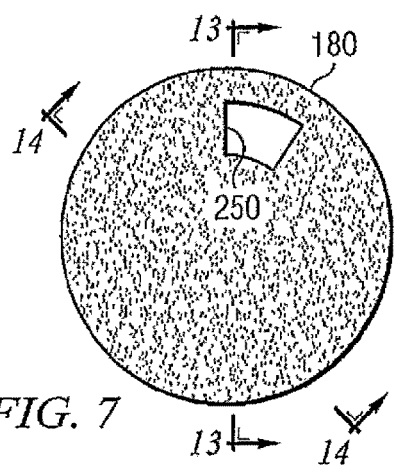
FIGS. 7-12 are top views of components of a breathing apparatus in accordance with an embodiment of the present disclosure.
Figure 8:
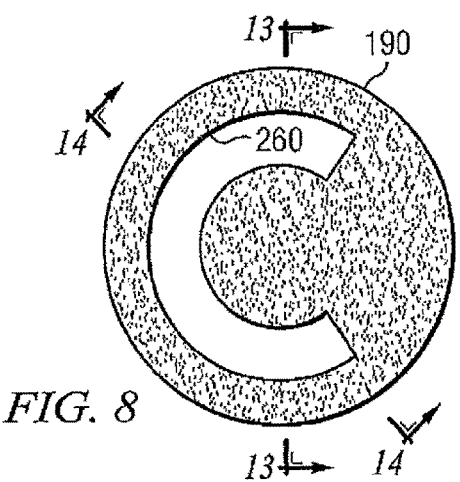
Figure 9:
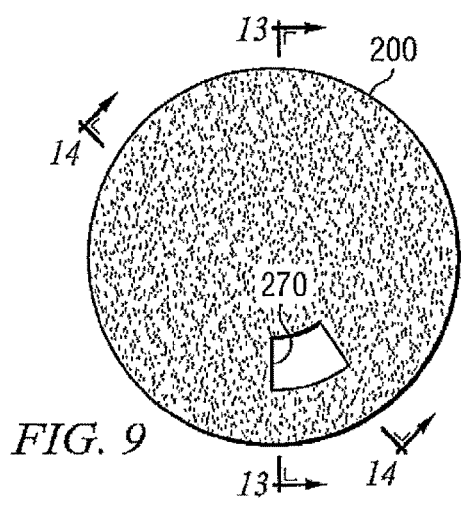
Figure 10:
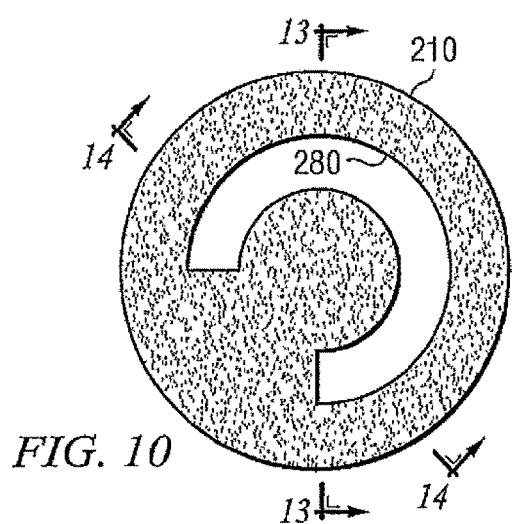
Figure 11:
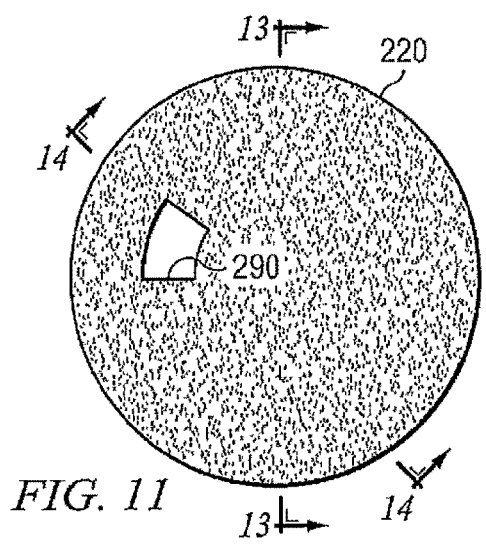
Figure 12:
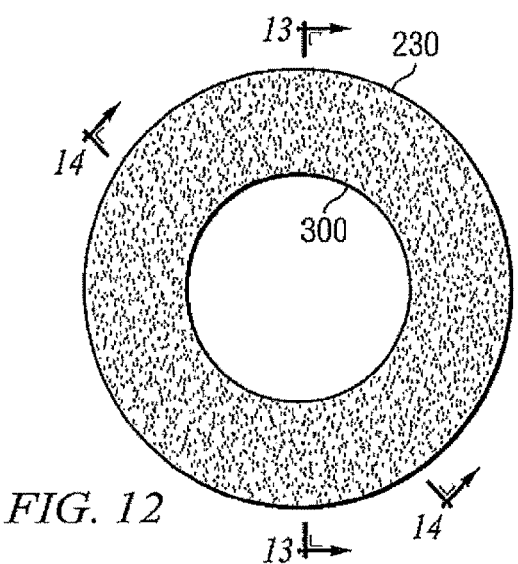

As discussed with reference to FIGS. 7-14, foam structure 150 may define a noise-suppressive conduit that channels gas from the ambient environment (e.g., adjacent aperture 250, as shown in FIG. 7) to the intake of the blower 310 (shown in FIG. 14). As generally used herein, a "noise suppressive conduit" may provide noise suppression through the use of the acoustic foam (or other noise suppressing) material forming the conduit walls, which absorb at least a portion of the sound generated by the blower.

FIGS. 7-12 are top views of components of noise suppression portion 110 in accordance with an embodiment of the present disclosure. FIGS. 13 and 14 are sectional side views of noise suppression portion 110 taken though line 13-13 and line 14-14, respectively, of FIGS. 7-12.

As shown in FIGS. 7-12, in some embodiments, foam structure 150 may include a stacked structure including a plurality of foam disks 180, 190, 200, 210, 220, and 230 manufactured from an acoustic foam material selected for its ability to absorb sound waves in the audible range. In some embodiments, one or more of the foam disks may be manufactured from a material such as, for example, Soundfoam absorption foam, which is a polyester and urethane based material, manufactured by Soundcoat Company, which foam may have a density of 2 lb. per cubic foot. Other appropriate acoustic foam materials which may be compressed and which absorb sound in the audible range may also be used. In certain embodiments, the foam disks may have a thickness of about 0.5 inch and diameters that vary from about 3.25 inches to about 4.25 inches in diameter. When stacked as illustrated in FIGS. 13 and 14, foam structure 150 may define a spiral-like conduit 240 extending from an aperture 250 in disk 180, through a C-shaped channel 260 in disk 190, through an aperture 270 in disk 200, through a C-shaped channel 280 in disk 210, and through an aperture 290 in disk 220, which may be in communication with a blower 310 (indicated in dashed line). The blower, as known in the art, may provide a pressurized supply of gas to the user. One example blower useful in connection with some embodiments is the blower used with Puritan Bennett GK 420 CPAP. The airflow through foam structure 150 is indicated with arrows passing through the conduits in the foam structures, entering foam structure 150 as indicated by arrow A (see FIG. 13), and exiting foam structure 150 into the blower 310 as indicated by arrow B (see FIG. 14).

Foam disks 180, 190, 200, 210, 220, and/or 230 may be attached together with an adhesive as is known in the art, or may be otherwise attached in any other suitable manner. As illustrated in FIGS. 13-15, foam structure 150 may be compressed, such that the noise suppression portion 110 may be reduced from an uncompressed height 330 (FIG. 14) to a compressed height 340 (FIG. 15). In an example embodiment, uncompressed height 330 may be approximately 3.0 inches and compressed height 340 may be approximately 1.5 inches. It may be understood that foam structure 150 may include more or fewer foam disks than illustrated in FIGS. 7-15. Moreover, in some embodiments, foam structure 150 may be manufactured from a single piece of foam in which a conduit has been formed. The conduit may be substantially spiral in shape, serpentine, or may any other appropriate configuration.

Figure 16:
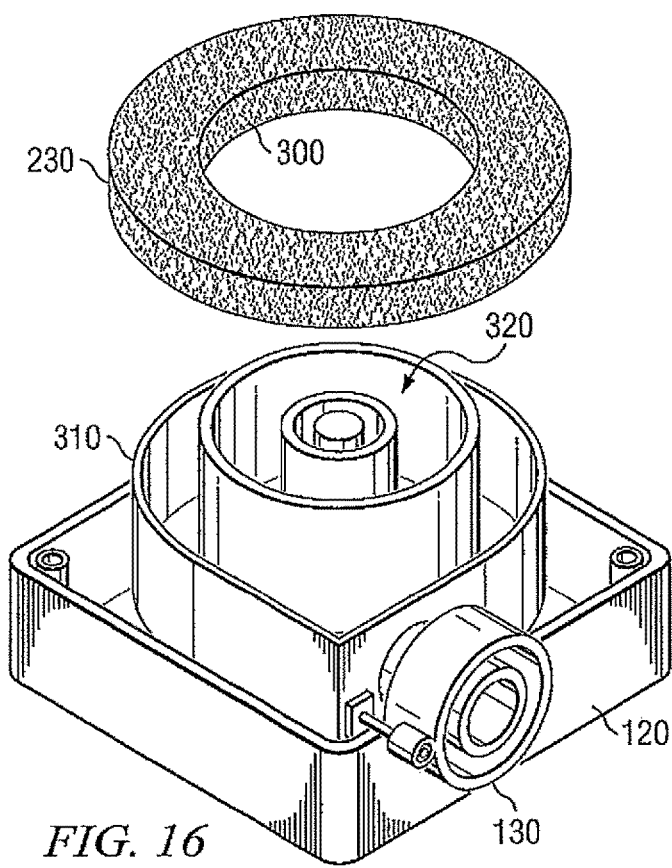
FIG. 16 is a perspective view, with parts separated, of a portion of a breathing apparatus in accordance with an embodiment of the present disclosure.
Figure 17:
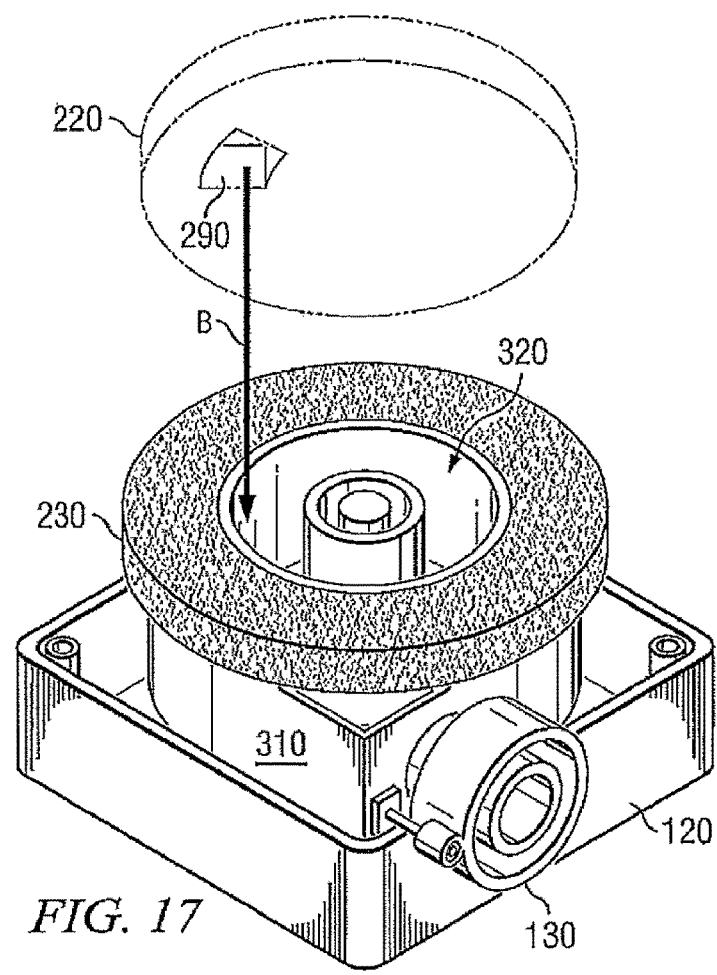
FIG. 17 is a perspective view of a portion of a breathing apparatus in accordance with an embodiment of the present disclosure.
Figure 18:
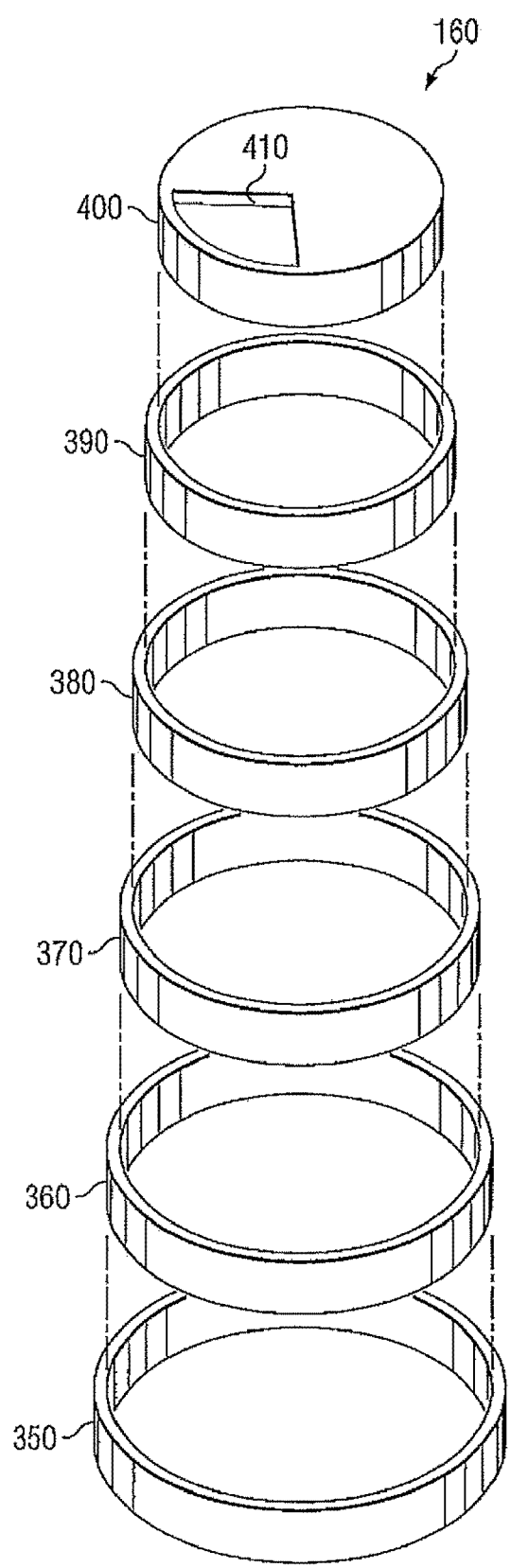
FIG. 18 is a view, with parts separated, of components of a breathing apparatus in accordance with an embodiment of the present disclosure.

As illustrated in FIGS. 16-17, foam structure 150 may be positioned over the blower such that the gas conduit may be in communication with the intake of the blower. In one embodiment, the lowest foam disk 230 may include an aperture 300 configured to be positioned over the blower 310. As illustrated in FIG. 18, foam disk 220 (illustrated with dashed lines) may be positioned over blower 320, such that aperture 290 aligns with the intake 320 of the blower 310.

Figure 19:
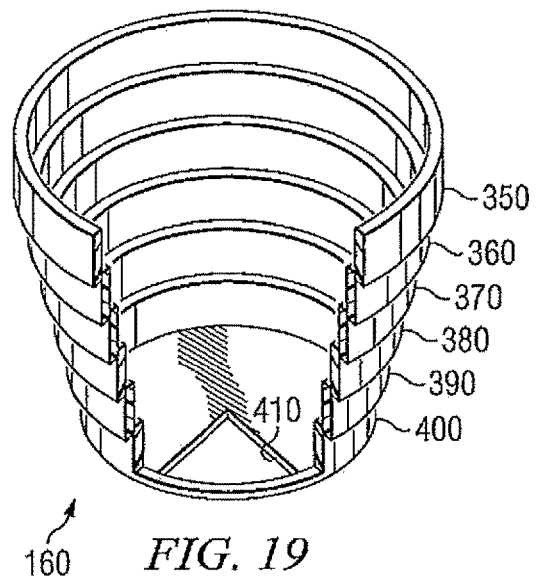
FIG. 19 is a perspective view from below of a portion of a breathing apparatus in accordance with an embodiment the present disclosure.

As illustrated in FIGS. 6 and 13-15, foam structure 150 may be encased by a shell 160. FIGS. 18-19 illustrate that shell 160 may include a plurality of concentric rings 350, 360, 370, 380, 390 and a cap 400 that may serve as a sound barrier between foam structure 150 and the environment. In addition, the shell 160 may provide mechanical support for foam structure 150. In one embodiment, shell 160 may also provide a mechanism for compressing foam structure 150 into the compressed configuration and/or to lock foam structure 150 in the compressed configuration (as illustrated in FIG. 16). One or more of the conical rings 350, 360, 370, 380, and 390 may be designed to be longitudinally slidable with respect to adjacent rings and may have an interference (e.g., frictional) fit with adjacent rings, which may allow the shell 160 to form a rigid structure and/or to be compressible when the noise suppression portion 110 is in the uncompressed and compressed configurations, respectively. Cap portion 400 may include an inlet 410. As illustrated in FIGS. 6 and 13, inlet 410 may align with aperture 250 in foam disk 180, and may allow gas to be drawn into the gas conduit in the foam structure 150 with relatively little flow resistance. Decreasing the flow resistance may reduce the work required by the blower.

The shell 160 may be manufactured from any rigid or semi-rigid material that can be formed in a ring or similar structure and which reflects sound waves, e.g., metals, plastics, and composites. It may be understood that the shell 160 may include more or fewer rings than illustrated herein. Moreover, shell 160 may alternatively include other collapsible structures, e.g., accordion configurations or flexible walls including struts or other supporting members when the foam is in the relaxed configuration.

Figure 20:
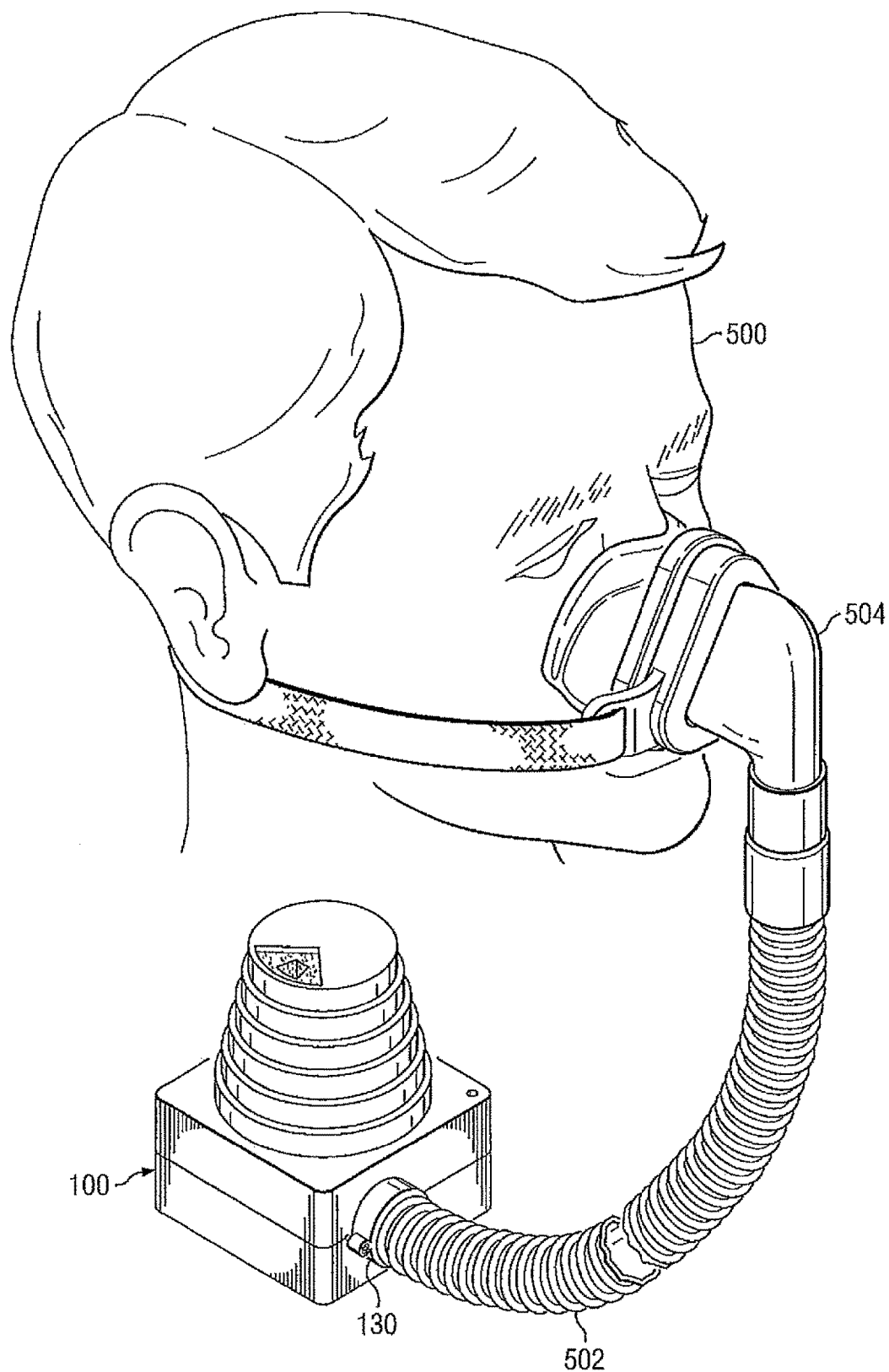
FIG. 20 illustrates an example breathing assistance system including a system including a noise suppression portion and coupled to a patient by a tube and nasal mask, according to one embodiment.

FIG. 20 illustrates a breathing assistance system including a system 100 including a noise suppression portion 110, a patient 500, and a tube 502 connected at one end to a port 130 of system 100 and at to the other end to a patent nasal mask 504.

While there have been described what are believed to be the preferred embodiments of the present disclosure, those skilled in the art will recognize that other and further changes and modifications may be made thereto without departing from the spirit of the disclosure, and it is intended to claim all such changes and modifications as fall within the true scope of the disclosure.

What is claimed is:

1. A system for delivering a supply of pressurized gas to a user, the system comprising:
   a blower having an intake portion and an outlet portion for supplying the pressurized gas to the user; and
   a noise suppression portion defining a conduit therethrough having an intake portion and an outlet portion, the outlet portion of said conduit in communication with the intake portion of said blower, wherein said noise suppression portion is moveable between a first configuration and a second configuration such that at least one exterior dimension of the system is reduced when the noise suppression portion is moved from the first configuration to the second configuration.

2. A system according to claim 1, wherein the first configuration of the noise suppression portion comprises an uncompressed configuration, and the second configuration of the noise suppression portion comprises a compressed configuration.

3. A system according to claim 1, wherein the noise suppression portion comprises a plurality of disks defining one or more openings therein.

4. A system according to claim 3, wherein at least one disk comprises foam.

5. A system according to claim 3, wherein the openings in adjacent disks are aligned to define the conduit.

6. A system according to claim 1, wherein the conduit defines a substantially spiral shape.

7. A system according to claim 1, further comprising a shell at least partially surrounding the noise suppression portion.

8. A system according to claim 7, wherein the shell is moveable between a first configuration having a first dimension and a second configuration having a second, reduced dimension.

9. A system according to claim 8, wherein the shell comprises a plurality of concentric rings.

10. A system according to claim 9, wherein the plurality of concentric rings are nested and longitudinally slidable with respect to adjacent rings.

11. A system according to claim 1 further comprising a tube having first and second ends, the first end of the tube adapted for connection to the outlet portion of the blower, and the second end of the tube adapted for connection to a mask.

12. A system according to claim 11 further comprising a mask adapted for connection to the second end of the tube.

13. A system according to claim 12, wherein the mask comprises a nasal mask.

14. An apparatus for reducing noise generated by a breathing device for delivering gas to a user, the system comprising:
   a body moveable between a first configuration and a second configuration such that at least one exterior dimension of the body is reduced when the body is moved from the first configuration to the second configuration; and
   a conduit defined within the body, the conduit having an intake portion and an outlet portion, the outlet portion of said conduit in communication with the intake portion of a gas supply device.

15. An apparatus according to claim 14, wherein the first configuration of a noise suppression portion is an uncompressed configuration, and the second configuration of the noise suppression portion is a compressed configuration.

16. An apparatus according to claim 14, wherein a noise suppression portion comprises a plurality of disks defining one or more openings therein.

17. An apparatus according to claim 16, wherein the disks are formed from foam.

18. An apparatus according to claim 16, wherein the openings in adjacent disks are aligned to define the conduit.

19. An apparatus according to claim 14, wherein the conduit defines a substantially spiral shape.

20. An apparatus according to claim 14, further comprising a shell at least partially surrounding a noise suppression portion.

21. An apparatus according to claim 20, wherein the shell is moveable between a first configuration having a first dimension and a second configuration having a second, reduced dimension.

22. An apparatus according to claim 21, wherein the shell comprises a plurality of concentric rings.

23. An apparatus according to claim 22, wherein the plurality of concentric rings are nested and longitudinally slidable with respect to adjacent rings.

24. A method, comprising:
providing a device for delivering a supply of pressurized gas to a user, the device including a blower having an intake portion and an outlet portion for supplying the pressurized gas to the user, and a noise suppression portion defining a conduit therethrough, said conduit having an outlet portion in communication with the intake portion of said blower; and
moving said noise suppression portion of said device between a first configuration and a second configuration such that at least one exterior dimension of the device is reduced when the noise suppression portion is moved from the first configuration to the second configuration.

25. A method according to claim 24, wherein:
the first configuration of the noise suppression portion is an uncompressed configuration, and the second configuration of the noise suppression portion is a compressed configuration; and
moving said noise suppression portion between said first and second configurations comprises compressing said noise suppression portion.

26. A method according to claim 24, wherein:
the noise suppression portion comprises a plurality of disks defining one or more openings therein; and
moving said noise suppression portion between said first and second configurations comprises sliding at least one of the disks relative to at least one of the other disks.

27. A system for delivering a supply of pressurized gas to a user comprising:
blowing means having an intake portion and an outlet portion for supplying the pressurized gas to the user; and
noise suppression means defining a conduit therethrough having an intake portion and an outlet portion, the outlet portion of said conduit in communication with the intake portion of said blowing means, wherein said noise suppression means is moveable between a first configuration and a second configuration such that at least one exterior dimension of the device is reduced when the noise suppression means is moved from the first configuration to the second configuration.

28. A system according to claim 27 further comprising a fluid communication means having first and second ends, the first end adapted for connection to the outlet portion of the blowing means, the second end adapted for connection to a mask.

29. A system according to claim 28, further comprising a mask.

30. A system according to claim 29, wherein the mask comprises a nasal mask.

* * * * *